United States Patent [19]

Lombardi

[11] Patent Number: 4,501,276
[45] Date of Patent: Feb. 26, 1985

[54] FETAL ELECTRODE APPARATUS

[75] Inventor: Edward J. Lombardi, Malden, Mass.

[73] Assignee: Illinois Tool Works Inc., Chicago, Ill.

[21] Appl. No.: 399,073

[22] Filed: Jul. 16, 1982

[51] Int. Cl.³ ............................................... A61B 5/04
[52] U.S. Cl. ..................................................... 128/642
[58] Field of Search ............... 128/642, 784, 785, 786, 128/419 P

[56] References Cited

U.S. PATENT DOCUMENTS

| | | | |
|---|---|---|---|
| Re. 28,990 | 10/1976 | Hon et al. | 128/642 |
| 3,750,650 | 8/1973 | Ruttgers | 128/642 |
| 3,754,555 | 8/1973 | Schmitt | 128/785 |
| 3,814,104 | 6/1974 | Irnich et al. | 128/785 |
| 3,835,864 | 9/1974 | Rasor et al. | 128/419 P |
| 3,844,292 | 10/1974 | Bolduc | 128/785 |
| 3,976,082 | 8/1976 | Schmitt | 128/785 |
| 4,066,085 | 1/1978 | Hess | 128/785 |
| 4,080,961 | 3/1978 | Eaton | 128/642 |
| 4,103,690 | 8/1978 | Harris | 128/785 |
| 4,112,952 | 9/1978 | Thomas et al. | 128/785 |
| 4,142,530 | 3/1979 | Wittkampf | 128/785 |
| 4,180,080 | 12/1979 | Murphy | 128/785 |
| 4,280,512 | 7/1981 | Karr et al. | 128/785 |
| 4,294,258 | 10/1981 | Bernard | 128/642 X |

FOREIGN PATENT DOCUMENTS

| | | | |
|---|---|---|---|
| 0004785 | 10/1979 | European Pat. Off. | 128/642 |
| 2738479 | 3/1979 | Fed. Rep. of Germany | 128/642 |

OTHER PUBLICATIONS

Syracuse et al., Annals of Biomedical Engineering 5, 362–366, (1977).

Primary Examiner—Lee S. Cohen
Attorney, Agent, or Firm—Thomas W. Buckman; John P. O'Brien

[57] ABSTRACT

An apparatus for use in monitoring fetal vital signs with monitoring equipment is disclosed. The apparatus includes a form sustaining guide tube, a sleeve, a fetal electrode structure having a piston member and a body member, at least two active fetal electrodes and a lead wire for connecting the active fetal electrodes to monitoring equipment. At least a portion of the guide tube and the body member are slideably disposed within the sleeve. The active fetal electrodes are attached to this piston member and their free ends are disposed within channels defined by the body member. The channels project arcuately outwardly by a predetermined radius of curvature so as to define a continuous outwardly advancing open passage through the body member. The body member also includes a shoulder to preclude movement of the body member within the sleeve by more than a predetermined distance. The apparatus is inserted through passages of a woman in labor brought into contact with the fetal scalp. By exerting pressure, the guide tube advances in the sleeve and releasably contacts the piston member which in turn advances the active fetal electrodes through and out of the channels with an outward curvature and into the fetal scalp.

52 Claims, 11 Drawing Figures

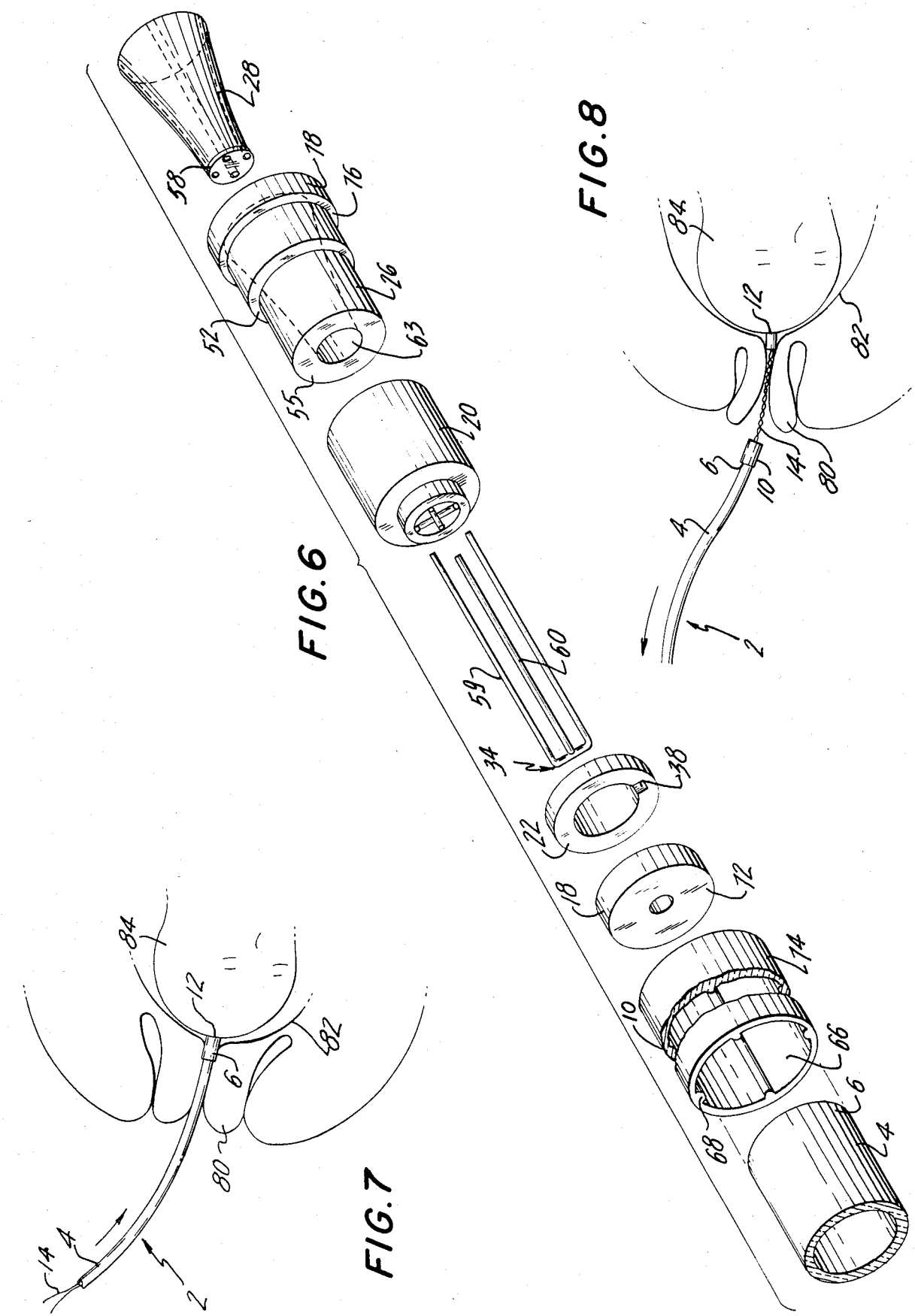

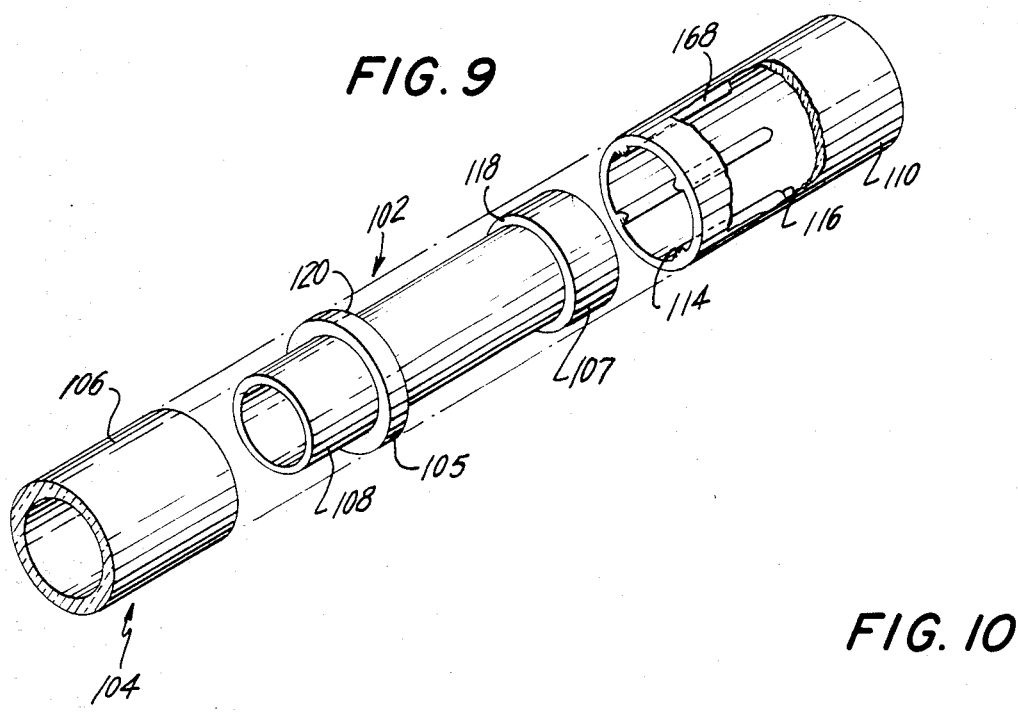
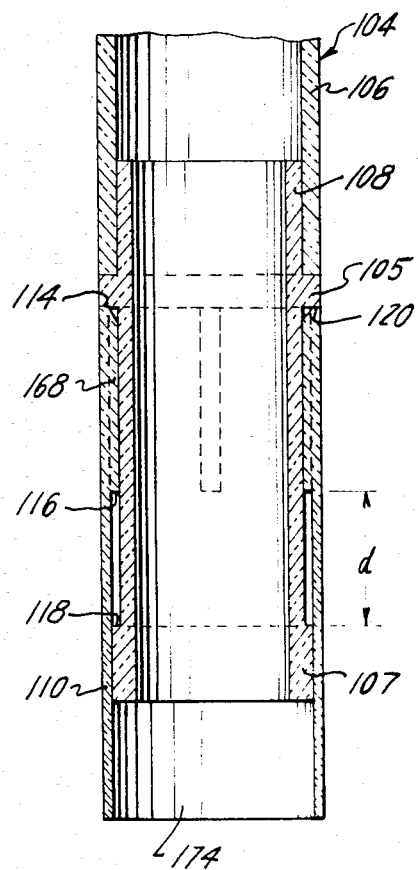
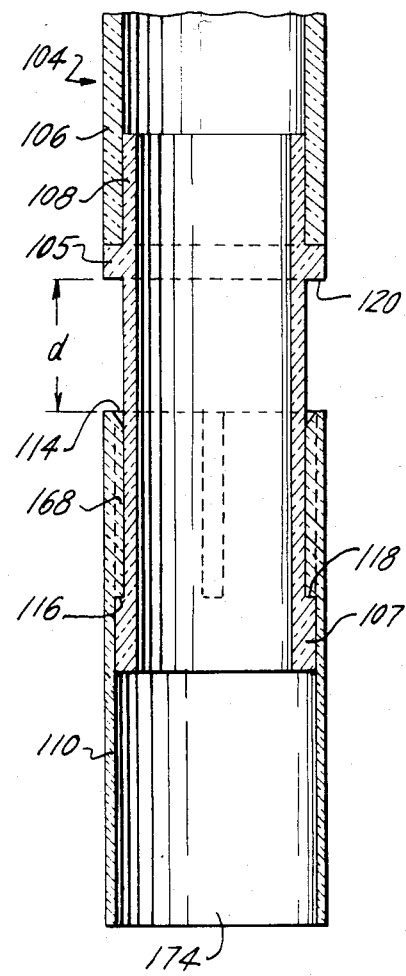

FETAL ELECTRODE APPARATUS

BACKGROUND OF THE INVENTION

1. Field of the Invention

This invention relates to a fetal electrode apparatus suitable for attachment to a fetus for prenatal examination and monitoring. More particularly, the invention relates to an improved bipolar electrode instrument adapted to be inserted through the vagina and cervix of a woman in labor and secured to a fetus for monitoring fetal heart rate.

2. Description of the Prior Art

During labor it is desirable to monitor continuously fetal physiological signals such as heart rate, pH and the like so as to be aware of the physical condition of the fetus. If the fetus is in distress, the baby can be delivered immediately by a caesarian section. Devices attached external to the mother's body have proven inadequate for monitoring of the fetus because they cannot distinguish clearly the fetal heart rate from that of the mother.

Various other devices have been developed for attachment directly to the fetus. For example, a forcep type electrode device has been used to obtain fetal heart rate. The forcep electrode device usually has pincher electrode clips secured to a plug which is placed at the end of a guide tube. The forcep electrode device is inserted through the passages of a woman in labor by the guide tube, and the clips are squeezed onto the fetal scalp. The guide tube is removed and the clips are connected to monitoring equipment by insulated wires. Disadvantageously, the clips are very brittle and are often cracked or damaged during application. The clips also are not rigidly positioned on the fetal scalp and can pivot about an axis defined by their points of fixation. Such cracking and pivoting of the electrode create electrical noise which interferes with fetal monitoring. Additionally, removal of the clips from the fetus often causes excessive trauma and injury. Upon removal of the clips, the fetal scalp may bleed excessively and the newborn would be susceptible to infections.

In another prior art apparatus, a spiral fetal electrode device has been used to obtain fetal heart rate readings. The device has one or two helical coils attached to a plug which in turn is mounted on the end of a flexible drive tube. An outer insertion tube slides around the drive tube. After inserting the spiral electrode device through the woman's passages and contacting the fetus, the coils are screwed into the fetal scalp by rotating the drive tube within the insertion tube. While inserting the spiral electrode device and rotating same onto the fetal scalp, the helical coils sometimes scrape the mother's tissues or become connected to the mother rather than to the baby. Consequently, the mother's tissues may be damaged or the mother's heartbeat may be read on the monitoring device rather than that of the baby. Additionally, the fragile helical coils occasionally break while being embedded within the fetal scalp. Furthermore, if the spiral fetal electrode device is not removed by carefully counter rotating the helical coils from the fetal scalp, significant trauma and injury can result. By the ripping of the fetal scalp due to improper removal of the spiral electrode, the fetus may sustain a serious scalp wound with significant bleeding and the newborn may become susceptible to infection.

SUMMARY OF THE INVENTION

This invention relates to an improved bipolar fetal electrode apparatus in which the disadvantages of the prior art are successfully avoided by providing an electrode instrument effecting firm, stable contact with the fetal scalp while minimizing trauma to the mother and baby during insertion or removal of the apparatus.

The fetal electrode apparatus comprises an insertion device having a form sustaining guide tube with a forward end portion and a sleeve; and a fetal electrode structure having a piston member, a body member, at least two active fetal electrodes and electrical lead means for connecting the active fetal electrodes to monitoring equipment.

The forward end portion of the guide tube and at least a portion of the fetal electrode structure are slideably disposed within the sleeve. The active fetal electrodes are attached to the piston member and free ends of the electrodes are disposed within channels defined by the body member. The channels provide a continuous open passage through the body member and they project radially outwardly by a predetermined radius of curvature as they advance through the body member. The body member also includes a shoulder means to preclude movement of the body member within the sleeve toward the piston member by more than a predetermined distance.

In accordance with the invention, the apparatus is inserted through the woman's passages and the fetal electrode structure contacts the fetal scalp. The guide tube slideably advances in the sleeve and releasably contacts the piston member. Due to this action, the piston member slides foward within the sleeve and the active fetal electrodes advance foward through and out of the channels with an outward curvature of a predetermined radius. The active fetal electrodes pierce the fetal scalp and generally advance outwardly along the plane of the scalp to effect firm, electrically conductive contact therewith.

The invention thus provides a safe and simple method for attaching a fetal electrode instrument onto a fetal scalp and subsequently removing the instrument without endangering the fetus. By minimizing injury to the fetal scalp, the fetal electrode instrument thus reduces the danger of excess bleeding and infection. While fixedly mounted in the fetal scalp, the inventive fetal electrode instrument possesses significant stability to overcome external forces acting upon the electrode due to the movement of the fetus or mother. With the fetal electrode apparatus of the present invention, the active fetal electrodes are in significant increased contact with the scalp yet do not injure the fetal skull. With all these conditions, accurate measuring signals of the fetal heart rate are obtained.

BRIEF DESCRIPTION OF THE DRAWINGS

Preferred embodiments of the invention are described hereinbelow with reference to the drawings wherein:

FIG. 6 is a perspective view of the various components of the fetal electrode apparatus of FIG. 1;

FIGS. 7 and 8 illustrate the manner in which the fetal electrode apparatus of the present invention is attached to a fetus;

FIG. 9 is a perspective view, partly in cross section, of another embodiment for the insertion device of the present invention;

FIG. 10 is a cross sectional view of the insertion device of FIG. 9 in a loaded position; and FIG. 11 is a cross sectional view of the insertion device of FIG. 9 in a released position.

DETAILED DESCRIPTION OF THE PREFERRED EMBODIMENTS

Figure 1:
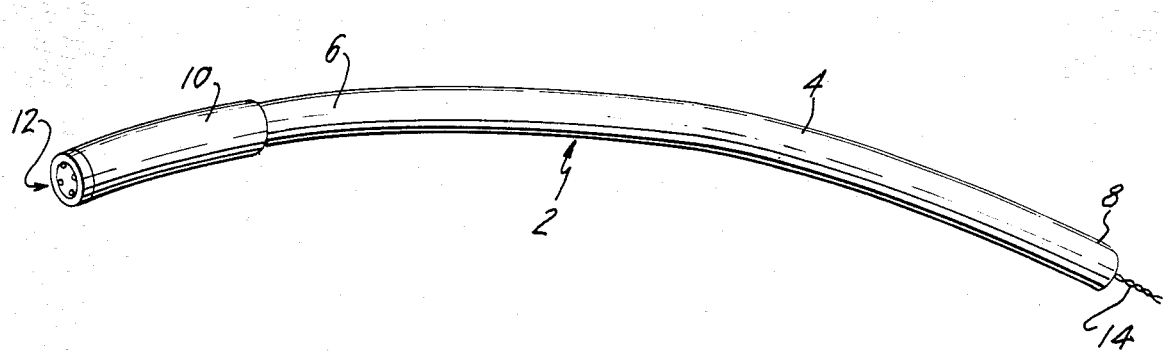
FIG. 1 is a perspective view of the fetal electrode apparatus of the present invention.

The present invention concerns an apparatus for use in monitoring fetal heartbeat. The apparatus includes an insertion device having a form sustaining elongated member or guide tube and a sleeve. The guide tube is adapted to be inserted through the vagina and cervix of a woman in labor. A sleeve having a forward end portion is disposed about a foward end portion of the guide tube and the sleeve is configured to allow slideable advancing of the forward end portion of the guide tube within the sleeve along the longitudinal axis of the sleeve.

The apparatus also includes a fetal electrode structure having a piston member, a body member with at least two channels, at least two active fetal electrodes and means for electrically connecting the active fetal electrodes to monitoring equipment. The piston member is slideably disposed within the sleeve for releasable contact with the forward end portion of the guide tube. The body member has a rearward portion and a forward portion. At least the rearward portion of the body member is releasably disposed within the sleeve and is positioned adjacent the piston member. The forward portion of the body member has a shoulder which is configured to demountably engage the forward end portion of the sleeve and preclude movement of the body member along the longitudinal axis of the sleeve toward the piston member by more than a predetermined distance. The forward portion of the body member is configured for releasably contacting a fetal scalp. The channels pass from the rearward portion of the body member and advance outwardly along the longitudinal axis of the sleeve through the forward portion of the body member. The channels define continuous open passages through the body member.

The flexible resilient active fetal electrode members are mounted on the piston member and are slideably disposed within the channels. The active fetal electrode members are of a sufficient length to pass through the channels and advance into the fetal scalp as the guide tube engages the piston member and causes the active fetal electrode members to advance along the channels and out of the forward portion of the body member.

In a preferred embodiment, a reference electrode is mounted on the piston member and means are provided for electrically connecting the reference electrode to the monitoring equipment.

In a preferred embodiment, the piston member is a head member or especially a cylinder member dimensioned to slideably advance within the sleeve along the longitudinal axis of the sleeve upon contact with and advancement of the guide tube in the sleeve. The head member defines a cavity having an opening adjacent the body member. The piston member also includes a cylindrical retainer cap adjacent the forward end portion of the guide tube for releasable contact therewith. The retainer cap is secured to the head member.

In a preferred embodiment of the invention, the rearward portion of the body member is a housing having an outer surface configured and dimensioned to fit within the cavity of the cylinder member in substantially sealed tight relation therewith. The housing also has a frustoconical inner wall with slots defining the channels. The forward portion of the body member is a plug member having a frustoconical outer wall for mating engagement with the inner wall of the housing.

In a preferred embodiment, there are four active electrode members and four channels passing through the body member. The active electrode members have free end portions which terminate in a beveled tip to facilitate piercing the fetal scalp. The channels are so defined by the slots in the inner wall of the housing such that the electrodes advance within the slots and exit the forward portion of the body member in a direction substantially parallel to the fetal scalp.

In an embodiment of the invention, the reference electrode comprises a flat metal disk secured to the piston member between the cylinder and the retainer cap member.

In another embodiment of the invention, the sleeve has an inner surface adjacent the guide tube with a multiplicity of projecting members such as ribs projecting radially inwardly so as to slideably contact the outer surface of the guide tube.

In a preferred embodiment, the insertion device also includes means for advancing the guide tube along the longitudinal axis of the sleeve by a predetermined distance in either direction.

FIG. 1 illustrates a fetal electrode apparatus 2 in accordance with the invention. Fetal electrode apparatus 2 includes an insertion device having a cylindrical, retractable, flexible, form-sustaining guide tube 4 with a forward end portion 6 and a rearward end portion 8, and a cylindrical sleeve 10; and a fetal electrode structure 12 with two insulated lead wires 14.

At least a portion of fetal electrode structure 12 is removably disposed within sleeve 10 and sleeve 10 slideably surrounds end portion 6 of guide tube 4. Lead wires 14 are electrically connected to fetal electrode structure 12. The lead wires pass through sleeve 10 and guide tube 4, out rearward end portion 8 and electrically connect to fetal monitoring equipment (not shown). Guide tube 4 is approximately 30 cm long and sleeve 10 is approximately 3 cm long.

Figure 2:
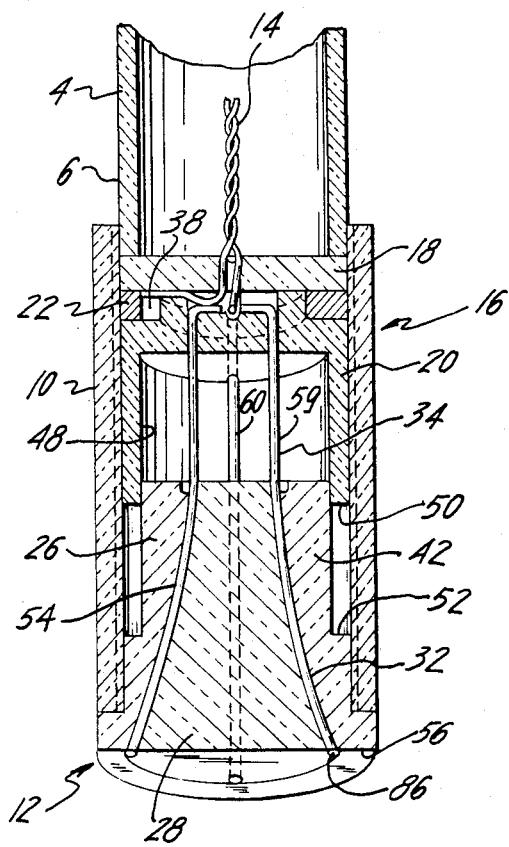
FIG. 2 is a perspective cross sectional view of the front portion of the fetal electrode apparatus of FIG. 1.

Referring to FIGS. 2-5, there is illustrated fetal electrode structure 12 having a displaceable piston member 16 with a retainer cap 18 and a cylinder member 20; reference electrode 22; a body member 24 with a housing 26, a plug member 28 and four channels 32; four active fetal electrodes 34 and two insulated wires 14. FIG. 2 also shows sleeve 10 and forward portion 6 of guide tube 4 in releasable contact with retainer cap 18.

In piston member 16, retainer cap 18 has a cylindrical configuration with a central opening (similar to a washer) through which pass lead wires 14. Reference electrode 22 has a disk like configuration with a central opening and a slot 38 (similar to a slotted washer). Reference electrode 22 is positioned on cylinder member or head 20 to surround a surface extension 36. One of electrical lead wires 14 is soldered to reference electrode 22 in slot 38 for effecting electrical contact with the monitoring equipment. Retainer cap 18 is ultrasonically welded or glued to surface extension 36. Retainer cap 18 secures reference electrode 22 between retainer cap 18 and cylinder member 20.

In cylinder member 20, there is defined a hollow cavity 40 in which at least an upper portion 42 of housing 26 can be slideably disposed. Cylinder member 20 also has four passages 44 through which pass and in which are retained the four active fetal electrodes 34. Piston member 16 is configured and dimensioned to slide within sleeve 10 along the longitudinal axis of the sleeve.

In body member 24, the upper portion 42 of housing 26 is configured and dimensioned to slideably engage an inner wall 48 of cylinder member 20 so that cylinder member 20 can advance forward along the longitudinal axis of sleeve 10 and surround upper portion 42 to effect a sealed tight relation between cylinder member 20 and housing 26. Cylinder member 20 advances along upper portion 42 until end 50 of cylinder member 20 contacts surface 52 of body member 24. The sealed tight relation of cylinder member 20 with housing 26 precludes body fluids of the mother from entering cavity 40 and causing a grounding of active fetal electrodes 34 with reference electrode 22.

Housing 26 has an inner wall 54 with a frustoconical curved configuration. More specifically, inner wall 54 tapers radially outwardly from an internal face 55 as it advances to an external face 56 at a curvature of a predetermined radius. Inner wall 54 has four slots which follow the configuration of the inner wall from internal face 55 to external face 56. The four slots are arranged on external face 56 around an axis of radial symmetry. Plug member 28 has an outer wall 57 with a frustoconical curved configuration of the same radius as that of inner wall 54 of housing 26 so that inner wall 54 and outer wall 57 engage in mating relation. Inner wall 54 and the slots in outer wall 57 thereby define channels 32. Plug member 28 includes an integral snap ring 58 which snaps plug member 28 into housing 26. Alternatively, plug 28 can be ultrasonically welded or glued to housing 26.

Figure 3:
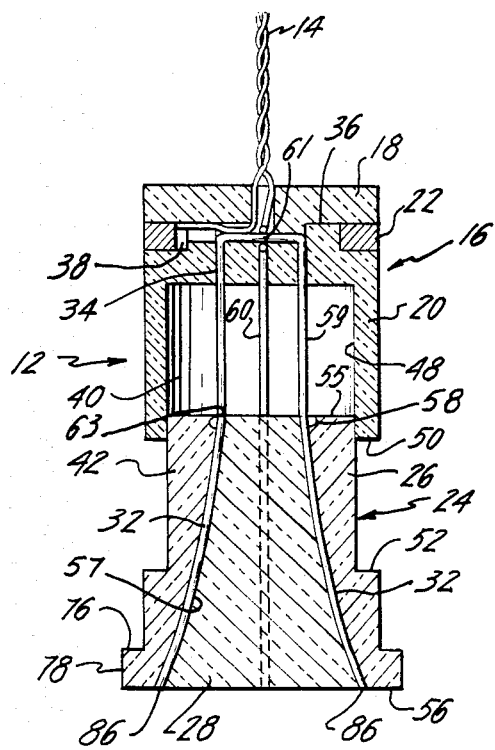
FIG. 3 is a cross sectional view of the fetal electrode structure of the present invention in a loaded position.
Figure 4:
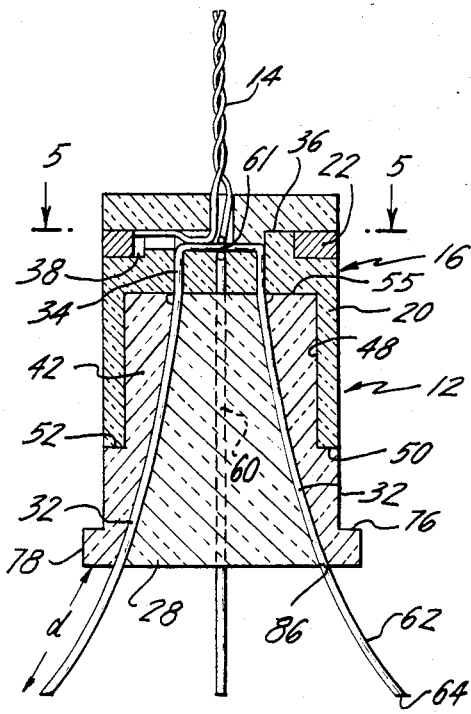
FIG. 4 is a cross sectional view of the fetal electrode structure of FIG. 4 in a released position.
Figure 5:
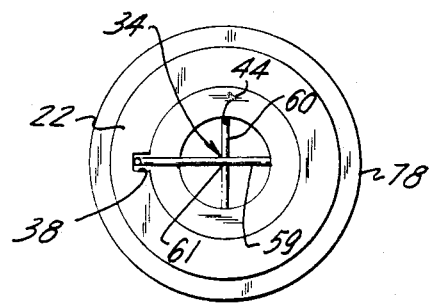
FIG. 5 is a cross sectional view taken along lines 5—5 of FIG. 4.

In the inventive apparatus, four active fetal electrodes 34 are made from two flexible, resilient U-shaped wires 59 and 60 which pass through cylinder member 20 via passages 44 and are soldered together along with one of lead wires 14 at position 61. Active fetal electrodes 34 are fixedly retained within piston member 16 by retainer cap 18. Each of the four active electrodes 34 have free ends 62 which pass through opening 63 in housing 26. Each active electrode 34 enters its own channel 32 and follow the configuration of the channel through housing 26. As seen in FIG. 3, in the loaded or retracted position, free end 62 of each active fetal electrode 34 terminates within body member 24. As seen in FIG. 4, free ends 62 of active fetal electrodes 34 project out from external face 56 by a distance "d" and have sharp beveled tips 64 for facilitating piercing a fetal scalp. The flat surface of beveled tip 64 projects toward the fetal scalp (not shown) with the point projecting outwardly to further effect outward advancement of the electrodes in a plane substantially parallel to the fetal scalp.

Referring to FIG. 6 there is disclosed the various elements of fetal electrode apparatus 2. There is shown guide tube 4, sleeve 10, retainer cap 18, reference electrode 22, active fetal electrodes 34, cylinder member 20, housing 26 and plug member 28.

As illustrated, forward end portion 6 of guide tube 4 releasably engages an inner surface 66 of sleeve 10 along ribs 68. Forward portion 6 of guide tube 4 slides within sleeve 10 along the longitudinal axis of sleeve 10 and releasably contacts an upper surface 72 of retainer cap 18. The dimensions of forward portion 6 and inner surface 66 are such that sliding therebetween is possible yet guide tube 4 preferably can be secured to sleeve 10.

Sleeve 10 has a forward end portion 74 which releasably surrounds a portion of housing 26 and releasably engages an upper surface 76 of flange or rim 78 of housing 26. Accordingly, at least a portion of housing 26 is releasably secured within sleeve 10 and the housing is precluded from moving more than a predetermined distance within sleeve 10 toward piston member 16 (i.e., retainer cap 18 and cylinder member 20) due to contact of forward end portion 74 with flange 78.

In the present invention, guide tube 4 and sleeve 10 preferably are made of synthetic plastic resins such as polyethylene. Retainer cap 18, housing 26 and plug member 28 preferably are made of synthetic plastic resins such as a machinable, injection moldable or extrudable polymers (e.g., nylon, polyvinyl chloride or acetals). Preferably, reference electrode 22 is made of an electrically conductive, non-corrosive, non-toxic material such as stainless steel. Preferably, active fetal electrodes 34 are made of electrically conductive, non-corrosive, non-toxic resilient materials such as spring stainless steel alloys. Advantageously, the same material is utilized for the reference electrode and the active fetal electrodes.

The method for using fetal electrode apparatus 2 of the present invention is illustrated with reference to the drawings, particularly FIGS. 1, 2, 7 and 8. A doctor loads lead wires 14 and fetal electrode structure 12 through sleeve 10 such that insulated lead wires 14 pass through guide tube 4 and exit rearward portion 8 thereof. If active fetal electrodes 34 extend out of body member 24, the doctor tugs on insulated wires 14 in a direction along guide tube 4 away from fetal electrode structure 12. Upper wall 76 of flange 78 thus releasably engages forward end portion 74 of sleeve 10. The active electrodes 34 in turn are pulled along in this direction and their free ends 62 are withdrawn within body number 24 so that they do not extend out of face 56. This loaded or retracted position is shown in FIGS. 1, 2 and 3.

With the fetal electrode apparatus 2 in the loaded position, the doctor inserts forward section 6 of guide tube 4 through the mother's vagina 80 and cervix 82 as shown in FIG. 7. Fetal electrode structure 12 then is brought in contact with fetus 84. The doctor exerts a forward pressure along the longitudinal axis of guide tube 4 in a direction toward fetus 84. Consequently, forward portion 6 of guide tube 4 advances and releasably contacts retainer cap 18. With this forward pressure on retainer cap 18 and in turn upon cylinder member 20 (which contains active fetal electrodes 34) retainer cap 18 and cylinder member 20 slide forward within sleeve 10. Consequently, electrodes 34 advance through channels 32, out of openings 86 of face 56 and into the fetal scalp. Due to the predetermined radius of channels 32, the presence of beveled tips 64 of active fetal electrodes 34 and fetal skin resistance, the flexible electrodes generally advance in an outwardly direction substantially parallel to the fetal scalp.

When the doctor feels that guide tube 4 cannot advance any further, the electrode fetal structure is firmly secured to fetus 84. Fetal electrode apparatus 2 now is in the fully released or extended position as seen in FIGS. 2 and 4. That is, end 50 of cylinder member 20 has contacted surface 52 of housing 26 and active fetal electrodes 34 have advanced into the fetal scalp as far as permitted by the fetal electrode structure 12. For operability of fetal electrode apparatus 2, however, active fetal electrodes 34 do not have to be fully extended and inserted into the fetal scalp provided some contact with the scalp is maintained. Advantageously, channels 32 and body member 24 surround the non-extended portions of active electrode 34 to preclude contact with the mother's fluids and grounding out with reference electrode 22.

As seen in FIG. 8, after attaching the electrode fetal structure to fetus 84, the doctor exerts a rearward pressure on guide tube 4 in a direction away from fetus 84, and slides guide tube 4 together with sleeve 10 off of wires 14 leaving only fetal electrode structure 12 and wires 14 in the mother and attached to fetus 84. The free ends of lead wires 14 are then connected to suitable equipment for monitoring fetal heart rate (not shown).

Prior to actual delivery of the baby, it usually is desirable to remove fetal electrode structure 12 from fetus 84. This is accomplished in a simple, non-traumatic manner. The doctor grabs and pulls lead wires 14 in a direction away from the fetus and the mother's passages 80 and 82 thus removing fetal electrode structure 12 from fetus 84. More particularly, the force acting upon lead wire 14, acts upon piston member 16 and upon active fetal electrodes 34 pulling both away from fetus 84. Since active fetal electrodes 34 are located within arcuate channels 32 of body member 24 and are resilient, body member 24 will move with the electrodes away from fetus 84 upon application of the force. Because active fetal electrodes 34 are flexible, they will withdraw from the fetal scalp along the same path through which they entered, thus effecting minimal trauma to the fetus. There will only remain four small puncture wounds in the fetal scalp through which the active fetal electrodes 34 originally entered.

FIGS. 9–11 describe an alternate embodiment of the insertion device of the present invention. The insertion device includes a guide tube 104 having a front end portion 106, a hollow coupling member or junction member 102 having flanges 105 and 107, and sleeve 110 having ribs 168.

In junction member 102, a rear end portion 108 is firmly secured (e.g., force fit, gluing, etc.) within forward end portion 106 of guide tube 104. Flange 105 of junction member 102 contacts the end wall of forward end portion 106. Flanges 105 and 107 are separated by a distance at least sufficient for ribs 168 to slide therebetween. Preferably, flanges 105 and 107 are separated by a distance equal to the length of ribs 168 plus the distance ("d") active fetal electrodes 34 can extend out of fetal electrode structure 12.

When assembling the insertion device, sleeve 110 with its ribs 168 are slid over flange 107 of junction member 102 to a position between flanges 105 and 107. Advantageously, ribs 168 do not extend the full length of sleeve 110 but terminate in the sleeve as seen in FIG. 9. Preferably, end 114 of rib 168 is beveled toward the center of the sleeve to facilitate insertion of sleeve 110 about junction member 102 and flange 107.

As seen in FIGS. 10 and 11, ribs 168 slide between flanges 105 and 107 thus permitting sleeve 110 to move along member 102 by a predetermined distance in either direction along the axis of the sleeve. As shown in FIG. 10, end 116 of rib 168 slideably contacts end wall 118 of flange 107 to preclude further movement of the sleeve in a direction away from the junction member. Alternatively, end 114 of sleeve 110 slideably contacts end wall 120 of flange 105 to preclude further movement of sleeve 110 in a direction toward guide tube 104.

The method for using the insertion device of FIGS. 9–11 in conjunction with inventive fetal electrode structure 12 of FIGS. 2–4 is similar to that previously described with regard to FIGS. 1, 2, 7 and 8. In particular, the doctor loads lead wires 14 and fetal electrode structure 12 (not shown in FIGS. 9–11) into an end 174 of sleeve 110 such that lead wire 14 passes through junction member 102 and through and out a remote end (not shown) of guide tube 104. The doctor slides sleeve 110 in a forward direction toward fetal electrode structure 12 and away from guide tube 104. While grasping sleeve 110, the doctor tugs on insulated wires 14 in a direction along guide tube 104 away from fetal electrode structure 12. Upper wall 76 of flange 78 of fetal electrode structure 12 thus releasably engages end 174 of sleeve 110. If active fetal electrodes 34 of fetal electrode structure 12 extend out of body member 24, the doctor continues tugging on insulated wires 14 until the free ends of the active fetal electrodes withdraw within the body member. This loaded position for the insertion device alone is shown in FIG. 10.

With the fetal electrode apparatus in the loaded position, the doctor inserts foward end section 106 of guide tube 104 through the mother's vagina and cervix as shown in FIG. 7. As described previously, fetal electrode structure 12 is attached to the fetus and the insertion device is thus brought to a released position as seen in FIG. 11. The insertion device is removed in a manner described previously with regards to FIG. 8.

While the invention has been described in conjunction with certain embodiments, it is understood that various modifications and changes may be made without departing from the spirit and scope of the invention.

For example, guide tube 4 could be a flexible, form sustaining rod member. The slots which form channels 32 could be located in outer wall 57 of plug member 28 instead of in inner wall 54 of housing 26. An O ring could be secured around housing 26 between upper portion 42 and inner wall 48 to facilitate a sealed tight relation between housing 26 and cylinder member 20. Flange 78 on housing 26 may only project outwardly from housing 26 at certain locations instead of projecting around the entire circumference of housing 26, and forward end portion 74 of sleeve 10 may define slots to engage the modified flange 78. A ph electrode could be secured to plug member 28 and project toward the fetal scalp for contact therewith. Additionally, junction member 102 could be formed as an integral part of forward portion 106 of guide tube 104.

I claim:

1. An apparatus for use in monitoring fetal vital signs with monitoring equipment, insertable through the vagina and the cervix of a woman in labor into a fetal scalp, comprising:

(a) a form-sustaining guide tube having a forward end portion and adapted to be inserted through the vagina and cervix of the woman in labor;

(b) a sleeve having a forward end portion, the sleeve being disposed about the forward end portion of the guide tube, and the sleeve being configured to allow slideable movement of the forward end portion of the guide tube within the sleeve;

(c) a piston member slideably disposed within the sleeve for releasably engaging the forward end portion of the guide tube;

(d) a body member including:
(i) a rearward portion releasably disposed within the sleeve adjacent the piston member;
(ii) a forward portion having a shoulder releasably engaging the forward end portion of the sleeve and configured to preclude the forward portion of the body member from moving within the sleeve along the longitudinal axis of the sleeve toward the piston member by more than a predetermined distance, said forward portion of the body member effecting releasable contact with the fetal scalp; and
(iii) at least two channels passing from the rearward portion of the body member and advancing outwardly along the longitudinal axis of the sleeve through the forward portion of the body member, said channels defining continuous open passages through the body member;

(e) at least two resilient active electrode members mounted on the piston member and having a free end slideably disposed within the channels, said active electrode members being of sufficient length for the free ends to pass through the channels and advance into the fetal scalp as the guide tube engages the piston member and causes the active electrodes to advance along the channels and out of the forward portion of the body member; and (f) means for electrically connecting the active electrode members to the monitoring equipment.

2. The apparatus of claim 1 further comprising a reference electrode mounted on said piston member and means for electrically connecting the reference electrode to the monitoring equipment.

3. The apparatus of claim 2 wherein the piston member includes a head member dimensioned to slideably advance within the sleeve along the axis of the sleeve upon releasable contact with the guide tube.

4. The apparatus of claim 3 wherein the rearward portion of the body member includes a housing having a frustoconical configured inner wall with slots defining said channels.

5. The apparatus of claim 4 wherein the forward portion of the body member is a plug member having a frustoconical configured outer wall for mating engagement with the inner wall of the housing.

6. The apparatus of claim 5 wherein the inner wall of the housing and the outer wall of the plug member have a frustoconical, curved configuration which taper radially outwardly along the longitudinal axis of the sleeve from the rearward portion to the forward portion of the body member at a curvature of a predetermined radius.

7. The apparatus of claim 6 wherein the head member defines a cavity having an opening adjacent the body member.

8. The apparatus of claim 7 wherein the rearward portion of the body member is configured and dimensioned to fit within the opening and cavity of the head member in substantially sealed relation therewith.

9. The apparatus of claim 8 wherein the piston member further includes a retainer cap member for effecting releasable contact with the forward end portion of the guide tube and secured to the head member.

10. The apparatus of claim 9 wherein the channels are defined by the slots in the inner wall of the housing so that the electrodes exit the forward portion of the body member in radial symmetry.

11. The apparatus of claim 9 wherein the means for electrically connecting the active electrode members to the monitoring equipment includes an insulated wire electrically connected to the active electrode members.

12. The apparatus of claim 11 wherein the means for electrically connecting the reference electrode to the monitoring equipment includes an insulated wire electrically connected to the reference electrode.

13. The apparatus of claim 12 wherein there are four active electrode members and four channels passing through the body member.

14. The apparatus of claim 13 wherein the active electrode members have free end portions which terminate in beveled tips.

15. The apparatus of claim 14 wherein the reference electrode comprises a metal disk secured to the piston member.

16. The apparatus of claim 15 wherein the reference electrode is secured to the piston member between the head member and retainer cap member.

17. The apparatus of claim 16 wherein the sleeve has an inner surface adjacent the guide tube with a multiplicity of members projecting radially inwardly.

18. The apparatus of claim 17 wherein the projecting members are ribs.

19. The apparatus of claim 18 wherein the forward end portion of the guide tube has an outer surface which contacts the ribs of the inner surface of the sleeve, said outer surface and ribs being configured and dimensioned for retainably contacting each other yet allowing slideable movement along the longitudinal axis of the sleeve upon movement of the guide tube.

20. The apparatus of claim 19 wherein the sleeve and the piston member have a generally cylindrical configuration and the sleeve has an inside diameter greater than the outside diameter of the guide tube.

21. The apparatus of claim 20 wherein the body member is a synthetic resin plastic.

22. The apparatus of claim 21 wherein the piston member is a synthetic resin plastic.

23. The apparatus of claim 22 wherein the active electrodes are a spring stainless steel alloy.

24. The apparatus of claim 1 wherein the forward end portion of the guide tube includes a junction member slideably engaging the sleeve and for releasable contact with the piston member.

25. The apparatus of claim 24 wherein the junction member includes means for precluding movement of the junction member along the axis of the sleeve by more than a predetermined distance in both directions of movement.

26. A fetal scalp electrode apparatus for use with fetal monitoring equipment comprising:
(a) a sleeve;
(b) a form-sustaining guide tube having a forward end portion which is slideably disposed within the sleeve, said guide tube configured and dimensioned to pass through the vagina and cervix of a woman in labor;
(c) a piston member having a rearward end surface and a forward end surface and slideably disposed within the sleeve for the rearward end surface to releasably engage the forward end portion of the guide tube as the guide tube advances through the sleeve;

(d) at least two flexible, elongated active electrode legs, each attached to the piston member and having a free end projecting in a direction away from the guide tube;

(e) lead means for electrically connecting the active electrode legs to the monitoring equipment; and (f) a body member including:
  (i) an internal face disposed within the sleeve for releasably engaging the forward end surface of the piston member as the piston member and guide tube advance through the sleeve;
  (ii) an external face having a shoulder means releasably contacting the sleeve and precluding the body member from sliding within sleeve toward the piston member by more than a predetermined distance, said external face configured for releasably contacting the fetal scalp; and
  (iii) at least two channels, each channel surrounding a portion of the respective electrode leg and defining a continuous passage through the body member for slideable passage of the electrode leg therein, each channel having a predetermined curvature advancing outwardly from the internal face of the body member to the external face of the body member imparting on the active electrode leg an outwardly advancing curvature of a predetermined radius as the active electrode leg advances through the channel during the action of the guide tube on the piston member, said active electrode legs being of a sufficient length for the free ends to pass through the channels and out of the external face of the body member into the fetal scalp.

27. The apparatus of claim 26 wherein there are four active electrode legs and four channels.

28. The apparatus of claim 27 further comprising means for obtaining a sealed-tight relation between the piston member and the body member.

29. A fetal electrode apparatus for monitoring fetal heart rate with monitoring equipment comprising:

(a) a form-sustaining guide tube having a forward end portion and adapted to advance through the passage of a woman in labor and to be positioned adjacent to the fetus;

(b) a generally cylindrical sleeve member surrounding the forward end portion of the guide tube and configured for effecting slideable movement of the guide tube along the longitudinal axis of the sleeve member;

(c) a cylindrical piston member slideably disposed within the sleeve member adjacent the forward end portion of the guide tube and configured for releasable contact with the forward end portion of the guide tube and slideable advancement along the longitudinal axis of the sleeve member by the action of the guide tube;

(d) four flexible, electrically conductive, active electrodes connected to the piston member and projecting generally along the longitudinal axis of the sleeve member;

(e) insulated lead means for electrically connecting the active electrodes to the monitoring equipment;

(f) a reference electrode mounted on the piston member;

(g) insulated lead means for electrically connecting the reference electrode to the monitoring equipment; and (h) a body member having:
  (i) a rearward portion releasably disposed within the sleeve member adjacent the piston member;
  (ii) a forward portion with a shoulder releasably engaging the sleeve member and configured to permit movement of the body member along the axis of the sleeve in one direction by a predetermined distance, said forward portion effecting releasable contact with the fetus; and
  (iii) four channels defining continuous open passages through the body member, each channel slideably surrounding a portion of the respective active electrode and having an outwardly projecting curvature of a predetermined radius from the rearward portion to the forward portion of the body member for deflecting the electrode out of general alignment with the longitudinal axis of the sleeve member and imparting said curvature of the predetermined radius on the active electrode as the active electrode advances through the channel during the action of the guide tube on the piston member, said electrodes being of sufficient length for a portion thereof to pass out of the channels and contact the fetus.

30. The apparatus of claim 29 further comprising means for obtaining a sealed-tight relation between the piston member and the body member.

31. The apparatus of claim 30 wherein the forward end portion of the guide tube includes a junction member slideably engaging the sleeve member for releasable contact with the piston member.

32. The apparatus of claim 31 wherein the junction member includes means for precluding movement of the junction member along the axis of the sleeve by more than a predetermined distance in both directions of movement.

33. A fetal monitoring instrument comprising:

(a) an elongated member having a forward end portion and adapted to be inserted through a vagina and cervix of a woman in labor;

(b) a sleeve having a forward end portion, the sleeve being disposed about the forward end portion of the elongated member, and the sleeve being configured to allow slideable movement of the forward end portion of the elongated member within the sleeve along the longitudinal axis of the sleeve;

(c) a piston member slideably disposed within the sleeve for releasable contact with the forward end portion of the elongated member;

(d) a body member including:
  (i) a rearward portion releasably disposed within the sleeve adjacent the piston member;
  (ii) a forward portion having a shoulder releasably engaging the forward end portion of the sleeve and configured to preclude the forward portion of the body member from moving within the sleeve along the longitudinal axis of the sleeve toward the piston member by more than a predetermined distance, said forward portion of the body member configured for releasably contacting a fetal scalp; and
  (iii) at least two channels passing from the rearward portion of the body member and advancing arcuately outwardly through the forward portion of the body member, said channels defining continuous open passages through the body member; and (e) at least two resilient members mounted on the piston member and having free end portions slideably disposed within the channels, said resilient members being of sufficient length to pass through the channels and advance into the fetal scalp as the elongated member engages the piston member and causes the free end portions of the resilient members to advance along the channels and out of the forward portion of the body member, at least one of said resilient members being an electrode; and (f) means for electrically connecting the electrode to the fetal monitoring instrument.

34. A fetal scalp electrode structure for use with fetal monitoring equipment comprising:

(a) a piston member having a rearward end surface and a forward end surface;

(b) at least two resilient active electrode legs, each having one end attached to the piston member and a free end projecting in a direction away from the piston member;

(c) lead means for electrically connecting the active electrode legs to the monitoring equipment; and (d) a cylindrical body member including:
   (i) an internal end face disposed adjacent the piston member for releasably engaging the forward end surface of the piston member as the piston member advances toward the body member;
   (ii) an external end face having a shoulder projecting radially outwardly from the longitudinal axis of the body member, said external end face configured for releasably contacting the fetal scalp; and
   (iii) at least two channels, each channel surrounding a portion of the respective electrode leg and defining a continuous passage through the body member for slideable passage of the active electrode leg therein, each channel having a predetermined curvature advancing outwardly from the internal end face of the body member to the external end face of the body member imparting on the electrode leg an outwardly advancing curvature of a predetermined radius as the electrode leg advances through the channel due to the action of the piston member, said electrode legs being of a sufficient length for the free ends to pass through the channels and out of the external end face of the body member into the fetal scalp.

35. The fetal scalp electrode structure of claim 34 further comprising means for obtaining a sealed-tight relation between the piston member and the body member.

36. The apparatus of claim 35 wherein there are four active electrode legs and four channels.

37. An apparatus for use in monitoring fetal vital signs with monitoring equipment, insertable through the vagina and the cervix of a woman in labor into a fetal scalp, comprising:

(a) a form-sustaining guide tube adapted to be inserted through the vagina and cervix of the woman in labor;

(b) a junction member secured to an end of the guide tube;

(c) a sleeve having a forward end portion, the sleeve being disposed about the junction member, and the sleeve being configured to allow slideable movement of the junction member along the longitudinal axis of the sleeve;

(d) a piston member releasably disposed within the sleeve for sliding therein and releasably engaging the junction member;

(e) a body member including:
   (i) a rearward portion releasably disposed within the sleeve adjacent the piston member;
   (ii) a forward portion effecting releasable contact with the fetal scalp; and
   (iii) at least two channels passing from the rearward portion of the body member and advancing outwardly through the forward portion of the body member, said channels defining continuous open passages through the body member;

(f) at least two resilient, active electrode members mounted on the piston member and having free ends slideably disposed within the channels, said active electrode members being of sufficient length for the free ends to pass through the channels and advance into the fetal scalp as the junction member contacts the piston member and causes the active electrode members to advance along the channels and out of the forward portion of the body member; and (g) means for electrically connecting the active electrode members to the monitoring equipment.

38. The apparatus of claim 37 further comprising a reference electrode mounted on said piston member and means for electrically connecting the reference electrode to the monitoring equipment.

39. The apparatus of claim 38 further comprising means for advancing the junction member along the longitudinal axis of the sleeve by a predetermined distance.

40. The apparatus of claim 39 wherein the junction member slides within the sleeve and the sleeve has an inner surface adjacent the junction member with a multiplicity of rib members projecting radially inwardly.

41. The apparatus of claim 40 wherein the junction member advancing means includes a first flange positioned on the junction member and configured for engaging the rib members and precluding advancement of the junction member along the longitudinal axis of the sleeve in a direction by more than a predetermined distance.

42. The apparatus of claim 41 wherein the junction member advancing means further includes a second flange positioned on the junction member and spaced from the first flange, said second flange configured for engaging the rib members and precluding advancement of the junction member along the longitudinal axis of the sleeve in the other direction by more than a predetermined distance.

43. The apparatus of claim 42 wherein the forward portion of the body member has a shoulder releasably engaging the forward end portion of the sleeve and configured to preclude the forward portion of the body member from moving within the sleeve along the longitudinal axis of the sleeve toward the piston member by more than a predetermined distance.

44. A fetal electrode apparatus for monitoring the fetal heart rate with monitoring equipment comprising:

(a) form-sustaining guide tube having a forward end portion and adapted to advance through the passage of a woman in labor and to be positioned adjacent to a fetus;

(b) a hollow coupling member having an end fixedly secured within the forward end portion of the guide tube;

(c) a generally cylindrical sleeve surrounding the coupling member and configured for effecting slideable movement of the coupling member along the longitudinal axis of the sleeve;

(d) a cylindrical piston member slideably disposed within the sleeve adjacent the coupling member and configured for releasable contact with the coupling member and slideable advancement along the longitudinal axis of the sleeve by the action of the coupling member and guide tube;

(e) four flexible, electrically conductive, active electrodes connected to the piston member and having free ends projecting generally along the longitudinal axis of the sleeve in a direction away from the coupling member;

(f) insulated lead means for electrically connecting the active electrodes to the monitoring equipment;

(g) a reference electrode mounted on the piston member;

(h) insulated lead means for electrically connecting the reference electrode to the monitoring equipment; and (i) a body member having:
  (i) a housing, at least a portion being releasably disposed within the sleeve adjacent the piston member;
  (ii) a plug member secured within the housing, said plug member effecting releasable contact with the fetus; and
  (iii) four channels defining continuous open passages through the body member, the channels slideably surrounding a portion of the active electrodes and having an outwardly projecting curvature of a predetermined radius while passing through the body member for deflecting the electrodes out of general alignment with the longitudinal axis of the sleeve and imparting said curvature of the predetermined radius on the active electrodes as the active electrodes advance through the channels during the action of the guide tube and coupling member on the piston member, said electrodes being of sufficient length for their ends to pass out of the channels and into the fetal scalp.

45. The apparatus of claim 44 further comprising means for advancing the coupling member along the longitudinal axis of the sleeve by a predetermined distance.

46. The apparatus of claim 45 wherein the coupling member slides within the sleeve and the sleeve has an inner surface adjacent the coupling member with a multiplicity of rib members projecting radially inwardly.

47. The apparatus of claim 46 wherein the coupling member advancing means includes a first flange positioned on the coupling member and configured for engaging the rib members and precluding advancement of the coupling member along the longitudinal axis of the sleeve in a direction by more than a predetermined distance.

48. The apparatus of claim 47 wherein the coupling member advancing means further includes a second flange positioned on the coupling member and spaced apart from the first flange, said second flange configured for engaging the rib members and precluding advancement of the junction member along the longitudinal axis of the sleeve in the other direction by more than a predetermined distance.

49. The apparatus of claim 48 wherein the forward portion of the body member has a shoulder releasably engaging the sleeve and configured to preclude the forward portion of the housing from moving within the sleeve along the longitudinal axis of the sleeve toward the piston member by more than a predetermined distance.

50. An electrode apparatus for use with monitoring equipment, insertable through the vagina and the cervix of a woman in labor into a fetus, comprising:
(a) a sleeve;
(b) an elongated member having at least a forward end portion which is slideably disposed within the sleeve, said elongated member and sleeve configured and dimensioned to pass through the vagina and cervix of the woman;
(c) a piston member having a rearward end surface and a forward end surface and slideably disposed within the sleeve for the rearward end surface to releasably engage the forward end portion of the elongated member as the elongated member advances through the sleeve;
(d) at least two flexible, elongated active electrode legs, each leg attached to the piston member and having a free end projecting in a direction away from the elongated member;
(e) lead means for electrically connecting the active electrode legs to the monitoring equipment; and
(f) a body member including:
  (i) an internal face disposed within the sleeve for releasably engaging the forward end surface of the piston member as the piston member and elongated member advance through the sleeve;
  (ii) an external face having a shoulder means releasably contacting the sleeve and precluding the body member from sliding within sleeve toward the piston member by more than a predetermined distance; and
  (iii) at least two channels, each channel surrounding a portion of the respective electrode leg and defining a continuous passage through the body member for slideable passage of the electrode leg therein, each channel having a predetermined curvature advancing outwardly from the internal face of the body member to the external face of the body member imparting on the active electrode leg an outwardly advancing curvature of a predetermined radius as the active electrode leg advances through the channel during the action of the elongated member on the piston member, at least one of said active electrode legs being of a sufficient length for the free end to pass through the channel and out of the external face of the body member.

51. A fetal electrode apparatus for monitoring fetal heart rate with monitoring equipment comprising:
(a) an elongated member having a forward end portion;
(b) a sleeve member surrounding at least the forward end portion of the elongated member and configured for effecting slideable movement of the elongated member along the longitudinal axis of the sleeve member, said sleeve member and elongated member adapted to advance through the passage of a woman in labor and to be positioned adjacent to the fetus;

(c) a piston member slideably disposed within the sleeve member adjacent the forward end portion of the elongated member and configured for releasable contact with the forward end portion of the elongated member and slideable advancement along the longitudinal axis of the sleeve member by the action of the elongated member;

(d) at least four flexible, electrically conductive, active electrodes connected to the piston member and projecting generally along the longitudinal axis of the sleeve member;

(e) insulated lead means for electrically connecting the active electrodes to the monitoring equipment;

(f) a reference electrode mounted on the piston member;

(g) insulated lead means for electrically connecting the reference electrode to the monitoring equipment; and (h) a body member having:
  (i) a rearward portion releasably disposed within the sleeve member adjacent the piston member;
  (ii) a forward portion with a shoulder releasably engaging the sleeve member and configured to permit movement of the body member along the axis of the sleeve in one direction by a predetermined distance; and
  (iii) four channels defining continuous open passages through the body member, each channel slideably surrounding a portion of the respective active electrode and having an outwardly projecting curvature of a predetermined radius from the rearward portion to the forward portion of the body member for deflecting the electrode out of general alignment with the longitudinal axis of the sleeve member and imparting said curvature of the predetermined radius on the active electrode as the active electrode advances through the channel during the action of the elongated member on the piston member, at least one of said electrodes being of sufficient length for a portion thereof to pass out of the channel and contact the fetus.

52. An apparatus for use in monitoring fetal vital signs with monitoring equipment, insertable through the vagina and the cervix of a woman in labor into a fetal scalp, comprising:

(a) an elongated member having a forward end portion and adapted to be inserted through the vagina and cervix of the woman in labor;

(b) a sleeve having a forward end portion, the sleeve being disposed about at least the forward end portion of the elongated member and being configured to allow slideable movement of the forward end portion of the elongated member within the sleeve;

(c) a piston member slideably disposed within the sleeve for releasably engaging the forward end portion of the elongated member;

(d) a body member including:
  (i) a rearward portion releasably disposed within the sleeve adjacent the piston member;
  (ii) a forward portion having a shoulder releasably engaging the forward end portion of the sleeve and configured to preclude the forward portion of the body member from moving within the sleeve along the longitudinal axis of the sleeve toward the piston member by more than a predetermined distance; and
  (iii) at least two channels passing from the rearward portion of the body member and advancing outwardly along the longitudinal axis of the sleeve through the forward portion of the body member, said channels defining continuous open passages through the body member;

(e) at least two resilient active electrode members mounted on the piston member and having free ends slideably disposed within the channels, said active electrode members being of sufficient length for the free ends to pass through the channels and advance into the fetal scalp as the elongated member engages the piston member and causes the active electrode members to advance along the channels and out of the forward portion of the body member;

(f) means for electrically connecting the active electrode members to the monitoring equipment;

(g) a reference electrode secured to the piston member; and (h) means for electrically connecting the reference electrode to the monitoring equipment.

* * * * *

UNITED STATES PATENT AND TRADEMARK OFFICE
CERTIFICATE OF CORRECTION

PATENT NO. : 4,501,276
DATED : February 26, 1985
INVENTOR(S) : Edward J. Lombardi It is certified that error appears in the above—identified patent and that said Letters Patent is hereby corrected as shown below:

1. Cover sheet of captioned patent, first column, line 5, "Assignee: Illinois Tool Works Inc., Chicago, Ill." should read --Assignee: KONTRON INCORPORATED, EVERETT, MASSACHUSETTS--

2. Cover sheet of captioned patent, second column, lines 7-8, "Attorney, Agent or Firm - Thomas W. Buchman; John P. O'Brien" should read --Attorney, Agent or Firm - Jon S. Saxe, Bernard S. Leon and George W. Johnston--

Signed and Sealed this

Thirteenth Day of August 1985

[SEAL]

*Attest:*

DONALD J. QUIGG

*Attesting Officer*  *Acting Commissioner of Patents and Trademarks*